United States Patent
Clark et al.

(10) Patent No.: US 7,618,143 B2
(45) Date of Patent: Nov. 17, 2009

(54) PUPILOMETER

(75) Inventors: Andrew Clark, Boldon Colliery (GB); Iain R. Chambers, Cramlington (GB)

(73) Assignee: Newcastle-upon-Tyne Hospitals NHS Trust, Newcastle-upon-Tyne (GB)

( * ) Notice: Subject to any disclaimer, the term of this patent is extended or adjusted under 35 U.S.C. 154(b) by 296 days.

(21) Appl. No.: 10/540,766

(22) PCT Filed: Dec. 23, 2003

(86) PCT No.: PCT/GB03/05653

§ 371 (c)(1),
(2), (4) Date: Jun. 24, 2005

(87) PCT Pub. No.: WO2004/058056

PCT Pub. Date: Jul. 15, 2004

(65) Prior Publication Data

US 2006/0109422 A1 May 25, 2006

(30) Foreign Application Priority Data

Dec. 24, 2002 (GB) ................................ 0230223.0

(51) Int. Cl.
*A61B 3/10* (2006.01)
*A61B 3/00* (2006.01)
(52) U.S. Cl. ........................ 351/204; 351/243; 351/246
(58) Field of Classification Search ................. 351/204, 351/205, 206, 208, 213, 218, 221, 222, 243, 351/246
See application file for complete search history.

(56) References Cited

U.S. PATENT DOCUMENTS

| 4,755,043 | A | 7/1988 | Carter |
| 4,850,691 | A | 7/1989 | Gardner et al. |
| 5,490,098 | A | 2/1996 | Kardon |
| 5,573,006 | A | 11/1996 | Shimotani et al. |
| 5,790,235 | A | 8/1998 | Kirschbaum |
| 5,903,333 | A | 5/1999 | Siminou et al. |
| 5,953,097 | A | 9/1999 | Stark |
| 6,022,109 | A | 2/2000 | Dal Santo |
| 6,116,736 | A | 9/2000 | Stark et al. |
| 6,199,985 | B1 | 3/2001 | Anderson |
| 6,260,968 | B1 | 7/2001 | Stark et al. |
| 6,637,881 | B1 | 10/2003 | Siminou |
| 6,820,979 | B1 | 11/2004 | Stark et al. |
| 2006/0181678 | A1* | 8/2006 | Stark et al. .................. 351/206 |

FOREIGN PATENT DOCUMENTS

EP 0550673 7/1993
JP 2001178679 7/2001

* cited by examiner

*Primary Examiner*—Scott J Sugarman
*Assistant Examiner*—Brandi N Thomas
(74) *Attorney, Agent, or Firm*—Kinney & Lange, P.A.

(57) ABSTRACT

A pupilometer comprises image capturing means, illumination means comprising two spaced apart light sources, stimulation means, and image processing software, the illumination means generating and emitting light of a first wavelength, and the stimulation means generating and emitting light of a second wavelength. The illumination means is arranged to one or both sides of said image capturing means and, in use, shines light towards the eyeball, the image processing software receiving data from the image capturing means, and by processing said data according to an algorithm establishes the distance between the surface of the eyeball and the camera.

19 Claims, 15 Drawing Sheets

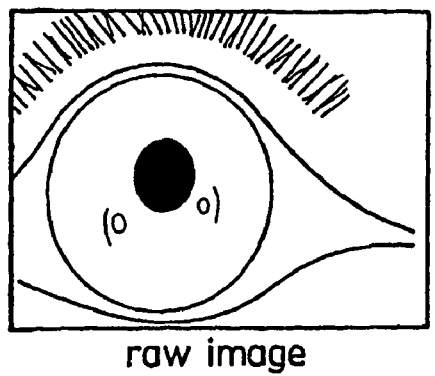
*Fig. 6*
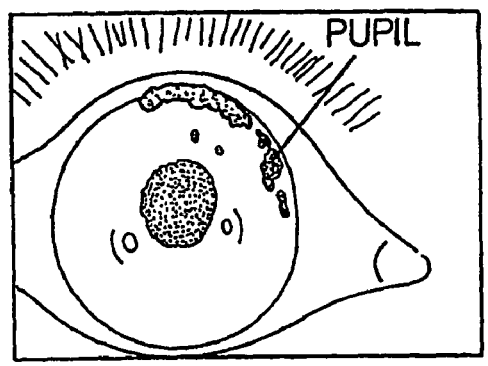
*Fig. 7*
| $P_0$ | $P_1$ | $P_2$ |
|---|---|---|
| $P_3$ | $P_4$ | $P_5$ |
| $P_6$ | $P_7$ | $P_8$ |
Where G is the magnitude of the gradient across target pixel $P_4$
*Fig. 8*
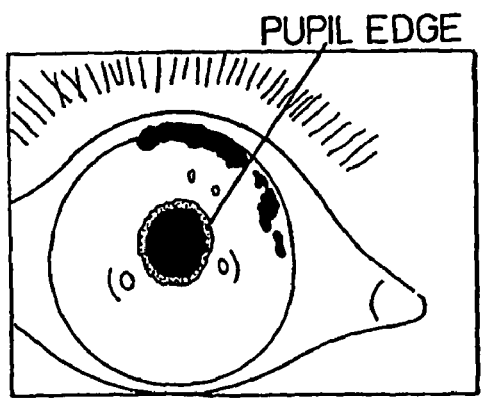
*Fig. 9*

PUPILOMETER

FIELD OF THE INVENTION

This invention relates to an apparatus commonly known as a pupilometer.

BACKGROUND OF THE INVENTION

In the neurological assessment of an unconscious patient, pupil response is known to be a vital aspect of the diagnostic process. Regular assessment of the size, reactivity to light and equality of pupils is essential for early recognition of neurological deterioration in situations where intra-cranial pathology is a threat. As such this assessment is regularly carried out in paramedic, intensive and high dependency care situations.

The current method of practice is to manually measure these aspects using a bright light, which stimulates reactivity of the pupil and make a note of the dilation compared to the original size of the pupil Actual measurements taken are then compared with a card having different pupil sizes mated thereon. This method of assessment is time consuming, and subjective.

Pupilometers have been developed for use in the assessment of eye shape and condition, monitoring tiredness, and in the detection of drugs or alcohol in a person.

A hand-held pupilometer is described in U.S. Pat. No. 6,022,109 Dal Sante). This pupilometer detects and measures pupil diameter and pupil response to a light stimulus. Also described is software to permit the diagnosis of alcohol or drug presence. However, use of this pupilometer requires the active participation of the user.

Another hand-held pupilometer is described in U.S. Pat. No. 6,199,985 (Anderson). This patent describes a method for measuring optical power output from the pupil. However, the pupilometer described in the patent requires complex optometric components.

Another hand-held pupilometer is described in U.S. Pat. No. 6,260,968 (Stark). The device described includes an LCD display via which prompts to the operator are given. The pupilometer described in this patent uses a "flying spot" algorithm to establish a circumference fitting the pupil, and the pupil radius. The pupilometer includes software to aid diagnosis. Again, the pupilometer described in this patent requires complex optometric components.

It would therefore be desirable to provide an improved pupilometer.

SUMMARY OF THE INVENTION

According to one aspect of the invention there is provided a pupilometer.

According to another aspect of the invention, there is provided image processing software.

The software may be embodied on a record medium, stored in a computer memory, embodied in read only memory, or carried on an electrical signal.

According to another aspect of the invention, there is provided a process for obtaining pupil image information.

According to another aspect of the invention, there is provided a hand-held pupilometer.

BRIEF DESCRIPTION OF THE DRAWINGS

In the drawings, which illustrate exemplary embodiments of pupilometers according to the invention:

FIG. 6 shows a raw image taken by the pupilometer before any image processing has taken place;

FIG. 7 shows the image of FIG. 6 after the identification of dark pixels;

FIG. 8 is a table used to identify an edge;

FIG. 9 shows the image of FIG. 7 after identification of the pupil edge;

DETAILED DESCRIPTION OF THE PREFERRED EMBODIMENTS

Figure 2:
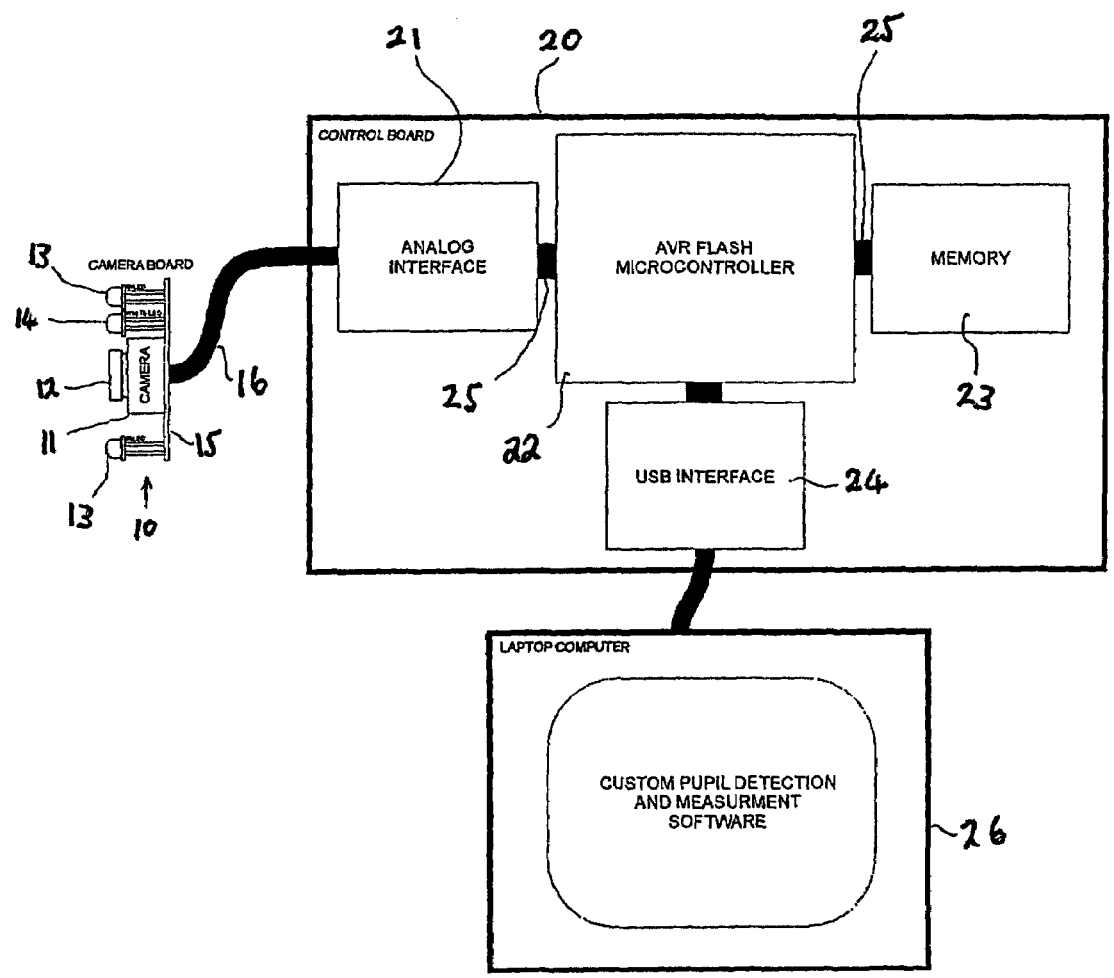
FIG. 2 is a block diagram of a pupilometer.

FIG. 2 illustrates the components of an embodiment of the pupilometer. The pupilometer comprises a camera board 10 including a camera, which in the example is a CMOS (Complementary Metal Oxide Semiconductor) camera 11, a filter 12, which in the example is an infra-red pass filter, a pair of infra-red light emitting diodes (IR LED's) 13, and a light emitting diode (LED) 14 for emitting white light The camera 11 and LED's 13, 14 are mounted on a board, which in the example is a printed circuit board 15, the filter 12 being mounted in front of the lens of the camera 11.

The camera board 10 is connected by suitable cabling to a control board 20, which mounts an analogue interface 21, a micro-controller 22, a memory 23 and a Universal Serial Bus (USB) interface 24. The analogue interface 21, memory 23 and USB interface 24 are each connected to the micro-controller 22 by suitable cabling 25. The analogue interface 21 receives an analogue video signal from the camera board 10 and converts said signal into a digital form The micro-controller 22 provides control signals for image acquisition from the camera board 10, and transmission of image data to a computer programmed with custom pupil detection and measurement software, which in the example is a laptop computer 26 connected to the micro controller 22 via a USB interface 24. However, the computer programmed with custom pupil detection and measurement software could easily form part of a hand held pupilometer device. Such a device is described with reference to FIGS. 20 to 22.

The control board 20 also mounts a memory module 23 which provides additional static RAM for storage of image data acquired from the camera board 10 prior to transmission of the image data to the computer 26, with the USB interface 24 providing a physical interface for the conversion and transmission of image frames to the computer 26 over a standard USB interface.

The computer 26 of the example runs the operating system, "Microsoft Windows 95", and custom software which detects and measures the pupil in the images generated by the camera.

Figure 3:
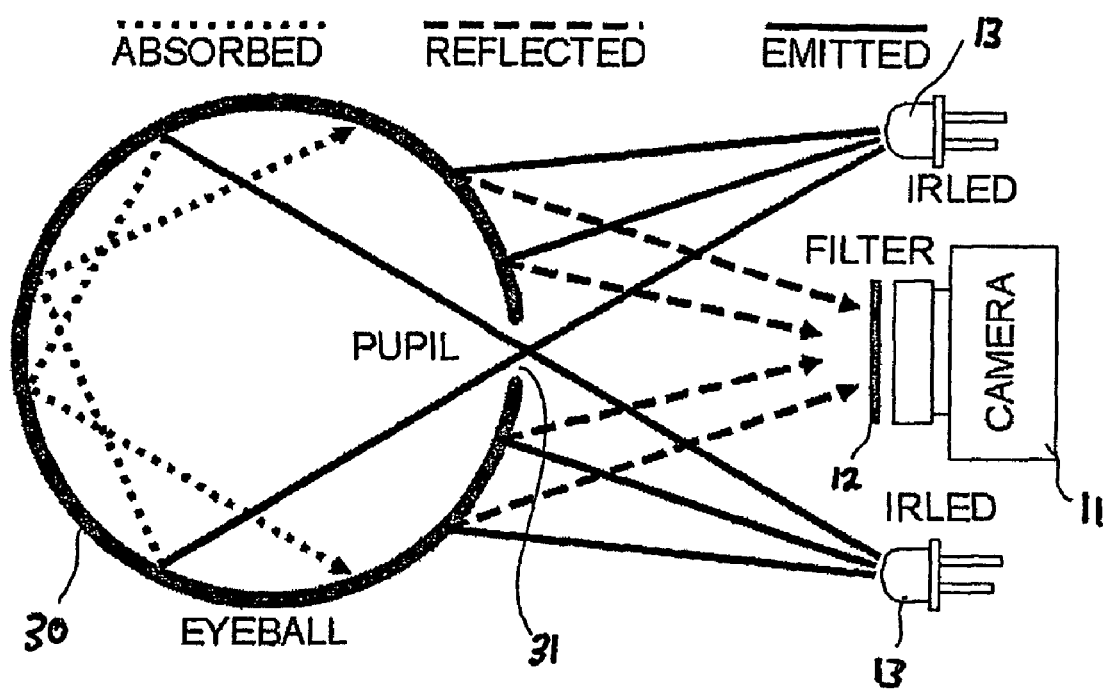
FIG. 3 is a schematic representation of an eyeball.

Referring now to FIG. 3, the IR LED's 13 shine light towards the eyeball 30, but to the sides of the pupil 31. By virtue of illuminating the eyeball by shining light to the sides of the pupil 31, most of the rays of light entering the pupil are internally reflected and absorbed by the retina, and thus the camera only sees light reflected from the surface of the eye, with the pupil appearing as a dark area.

The purpose of the infra-red pass filter 12 is to stop all visible light entering the camera 11, which eliminates the effects of ambient light conditions, thereby permitting accurate control of the instrument.

Figure 4:
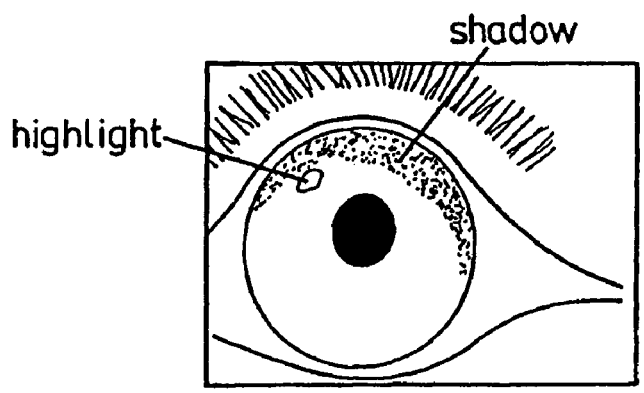
FIG. 4 is an image of an eye under ambient fight.
Figure 5:
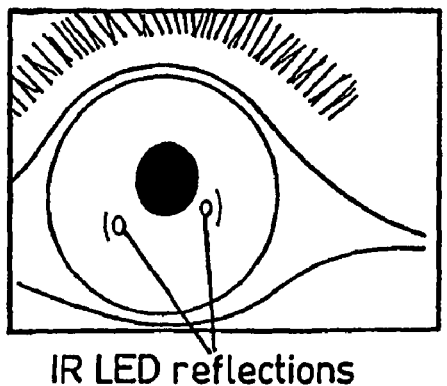
FIG. 5 is an image of an eye under infra-red light.

FIGS. 4 and 5 illustrate the difference in appearance of an eye under ambient light conditions (see FIG. 4) and infra red lights (see FIG. 5). In FIG. 5, the contrast between the pupil 3 and the iris 2 is increased compared to FIG. 4. Also, there is much less surrounding detail in FIG. 5 compared to FIG. 4.

The reflections from the IR LED's 13 can be seen clearly in FIG. 5, and the distance between these specular highlights is used as measure of the distance from the camera to the eye (the closer the IR LED's are to the eye, the further apart are the highlights).

Figure 23:
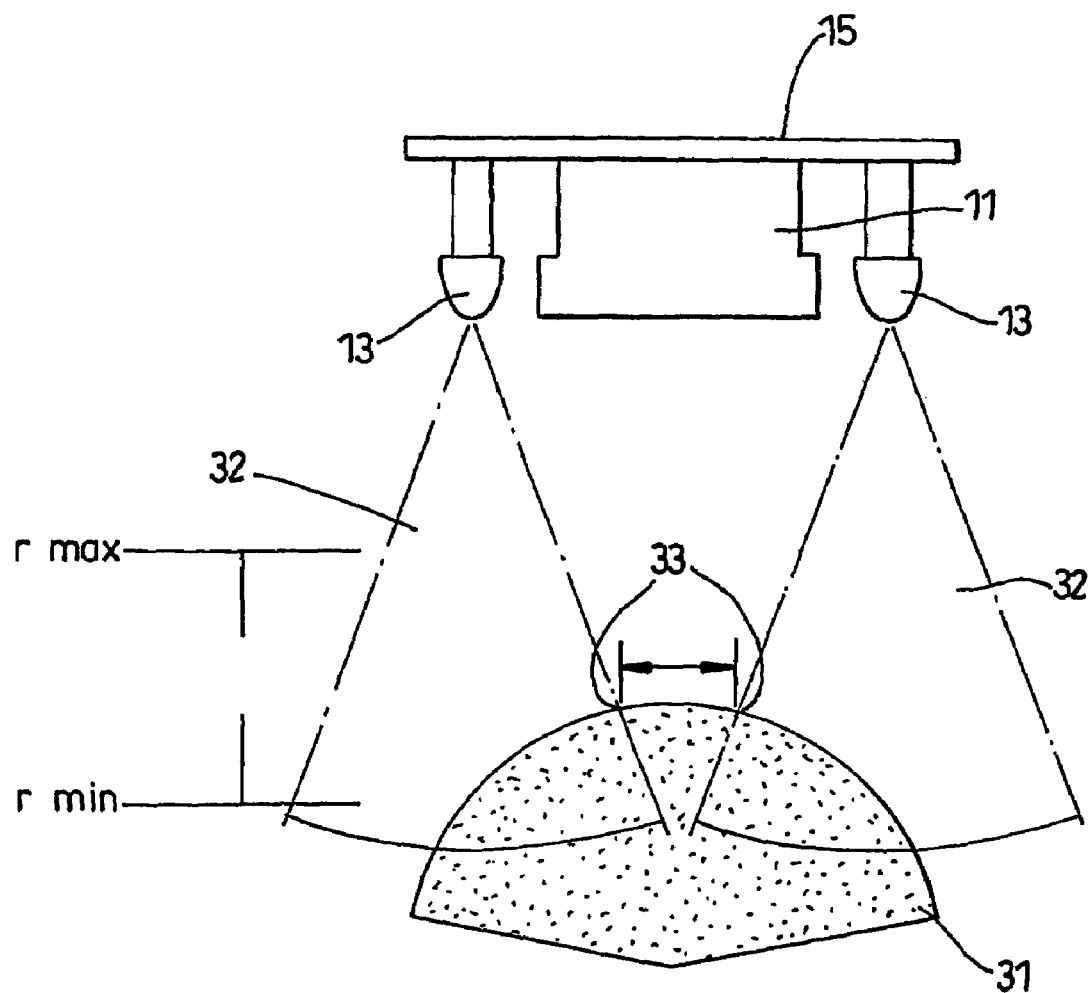
FIG. 23 is a schematic representation of a pupilometer of the invention in close proximity to an eye.

Referring now to FIG. 23, the eye 1 is illuminated by light in the infrared spectrum of light beams 32 emitted by the infrared LED's 13. The camera 11 sees highlights 33 on the surface of eyeball 30. For the pupilometer to generate an output of pupil size, separate highlights from each infra-red LED 13 must be detectable, and therefore must be within a certain distance of the surface of the eyeball. The extremes of the light beams 32 are illustrated by dotted lines. Clearly, if the infra-red LED's are too far away from the surface of the eyeball, they will overlap, in which case two spaced apart highlights 33 would not be appear on the surface of the eyeball. Conversely, if the infra-red LED's are too close to the surface of the eyeball, then the highlights will be so far apart as to be located in close proximity to the eyelids, rather than in the central region of the surface of the eyeball 30. In such a situation, the two highlights cannot be detected. Therefore, if the pupilometer is outside the range $r_{min}$-$r_{max}$, where $r_{min}$ is the minimum distance from the infra-red LED's to the surface of the eyeball 30, and $r_{max}$ is the maximum distance of the infra-red LED's to the surface of the eyeball 30, two separate highlights cannot be detected, and the pupilometer software produces a range error signal. The algorithm restarts the ranging step after pupil detection in the next captured image.

Figure 20:
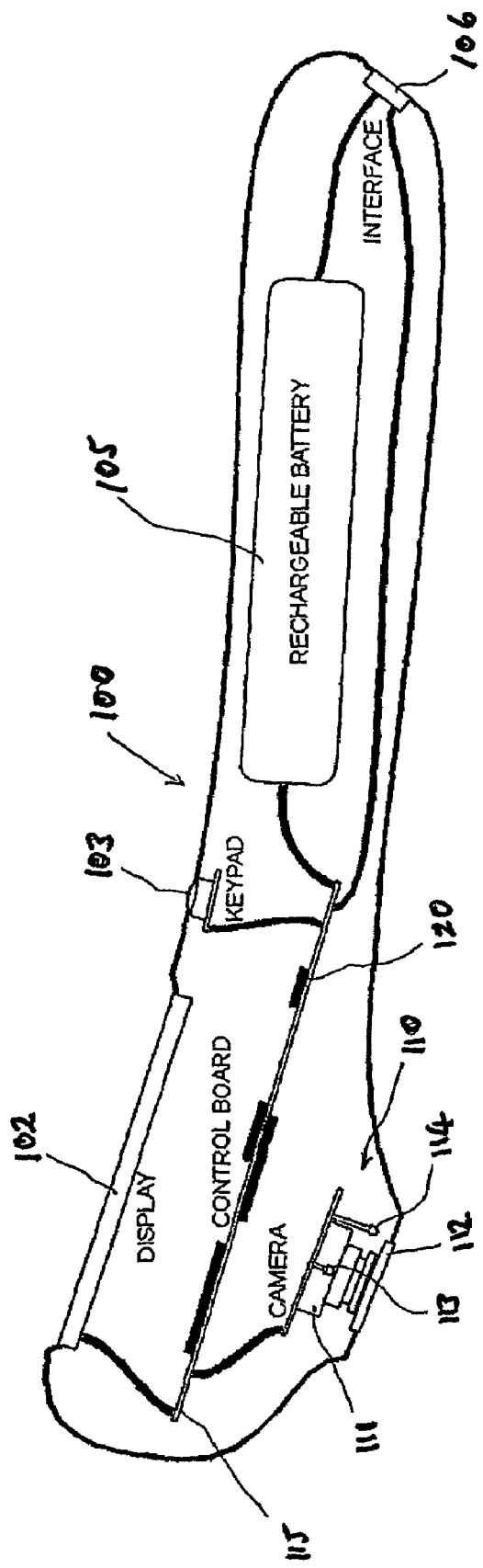
FIG. 20 is a schematic cross-section of a hand-held pupilometer.
Figure 21:
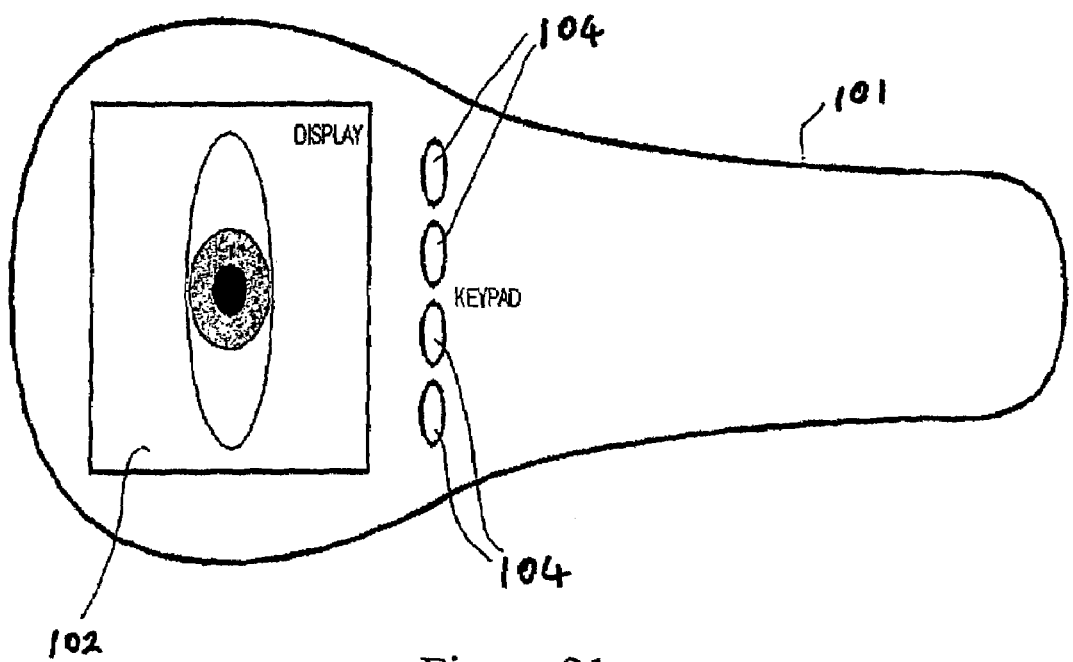
FIG. 21 is a plan view of the pupilometer illustrated in FIG. 20.
Figure 22:
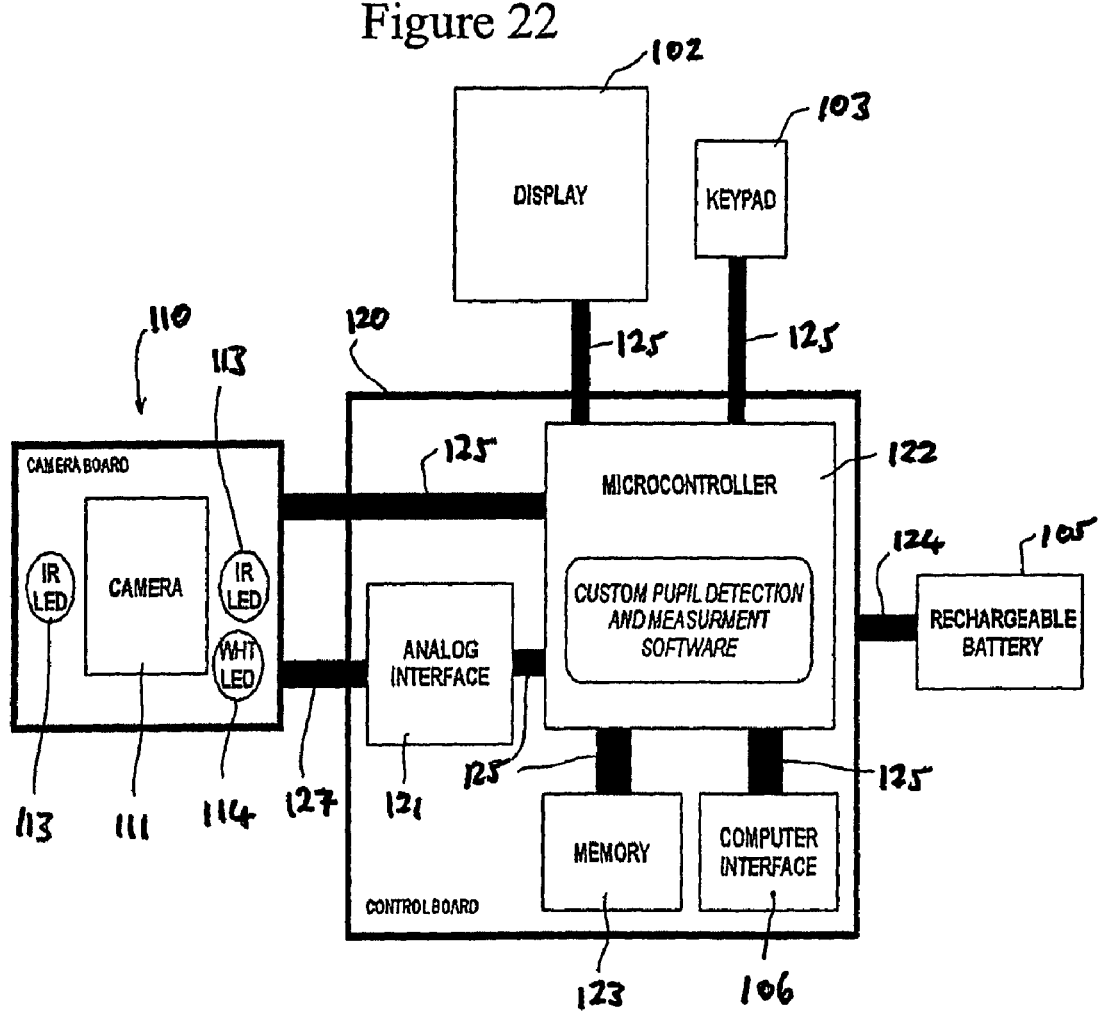
FIG. 22 is a block diagram of the pupilometer shown in FIGS. 20 and 21.

Referring now to FIGS. 20 to 22, there is shown a hand-held pupilometer, which comprises a camera board 110 including a camera, which in the example is a CMOS (Complementary Metal Oxide Semiconductor) camera 111, a filter 112, which in the example is an infra-red pass filter, a pair of infra-red light emitting diodes (IR LED's) 113, and a light emitting diode (LED) 114 for emitting white light The camera 111 and LED's 113, 114 are mounted on a board, which in the example is a printed circuit board 115, the filter 112 being mounted in front of the lens of the camera 111.

The camera board 110 is connected to a control board 120, which mounts an analogue interface 121, a micro-controller 122, a memory 123 and a computer interface 106. The analogue interface 121, memory 123 and computer interface 106 are each connected to the micro-controller 122 by suitable cabling 125. The analogue interface 121 receives an analogue video signal from the camera board 110 and converts said signal into a digital form The micro-controller 122 provides control signals for image acquisition from the camera board 110. Further, the microcontroller 122 transmits image data to, and runs, custom pupil detection and measurement software.

As mentioned above, the control board 120 also mounts a memory module 123 which provides additional static RAM for storage of image data acquired from the camera board 110 for use by the custom pupil detection and measurement software of the micro-controller.

The computer interface 106 provides a physical interface for transmission of data to an external computer. It may be desirable to store test results in patients' notes, or for research purposes, and whilst the hand-held device 100 has sufficient memory to record a number of results, to use the device continually, the memory 123 must be cleared from time to time.

As with the device described with reference to FIG. 3, the IR LED's 113 shine light towards the eyeball 30, but to the sides of the pupil 31. By virtue of illuminating the eyeball by shining light to the sides of the pupil 31, most of the rays of light entering the pupil are internally reflected and absorbed by the retina, and thus the camera only sees light reflected from the surface of the eye, with the pupil appearing as a dark area.

Pupilometer Software

The main function of the software is to interpret the image of the eye and detect, or classify, the pupil within that image. The software was developed using Borland Delphi and in the example executes under the Microsoft Windows operating system.

The basic requirement is the ability to detect a circle (i.e. the pupil) within the image and known algorithms available for the performance of this task include the Hough transform, parametric matching and neural network classification. However, these methods are computationally intensive and require a floating-point numeric processor in order to achieve optimal performance.

One aim of the invention to provide a standalone hand-held pupilometer. This means that a relatively low specification microprocessor must be used and therefore the algorithm of the invention is a simple multi-stage classification algorithm, which uses integer mathematical functions to classify the pupil within the image.

Figure 1:
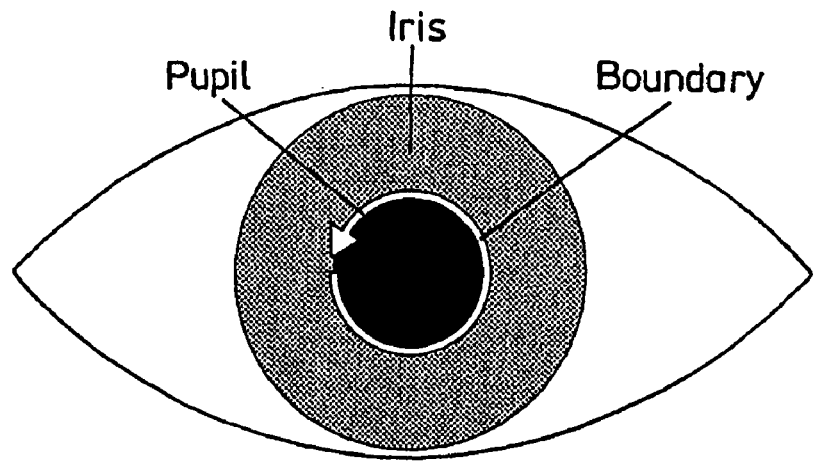
FIG. 1 is a schematic representation of a perfect eye.

Referring now to FIG. 1, there is shown a model of a perfect eye, i.e. the iris 2 is at the centre of the eyeball 1, with the pupil 3 being at the centre of the iris 2. Further, both the pupil 3 and the iris 2 are perfect circles, the boundary 4 between the iris 2 and the pupil 3 is sharp, and the darkest region of the eye is the pupil 3.

The software of the invention makes certain assumptions based on the model of the perfect eye described above, those assumptions being:
1) The pupil will be the darkest area of the image;
2) The pupil—iris boundary will have the sharpest edge;
3) The pupil—iris boundary will be elliptical.

The software provides three principal functions;
1. Pupil classification: the detection and measurement of the pupil within the image of the eye.
2. Ranging: the detection and measurement of the IR LED reflections on the eye surface allowing calculation of distance from camera to eye.
3. Stimulation: measurement of the pupil reflex action to light stimulation.

Pupil Classification

The classification algorithm of the invention provides for the differentiation of the pupil from other dark areas of the image, such as shadows, and from interference within the pupil boundary, for example eyelashes and highlights.

Figure 10:
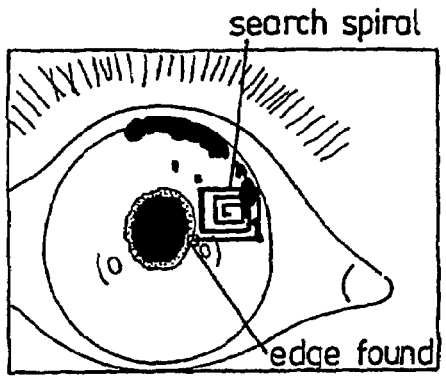
FIG. 10 shows the image of FIG. 9 at the beginning of a spiral search.
Figure 11:
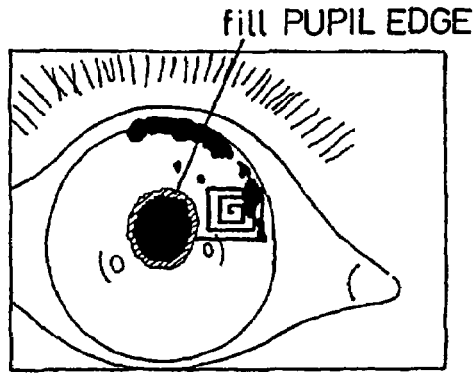
FIG. 11 shows the image of FIG. 9 with adjoining pupil edge pixels connected to one another.

The control board 20 transmits a new image every 200 ms via the USB interface 24. The image is returned as a two-dimensional (128×128 pixel) array of 6 bit values, with each value representing the greyscale intensity of the relevant image pixel in the range 0 to 63. This image is then subjected to the following processing steps:
1) As the raw image array is read into the Delphi program, the values of the darkest (Vdark) and the lightest (Vlight) pixels are calculated and stored. Threshold levels are then calculated using these values; Tdark=Vdark+4 and Tlight=Vlight−2—see FIG. 6.
2) All image pixels with values of less than or equal to this dark threshold (Td) are assigned to the PUPIL class—see FIG. 7.
3) The edge values across each of these PUPIL class pixels are calculated using the simple gradient algorithm |P4−P0|+|P4−P1|+|P4−P2|+|P4−P5|+|P4−P8|+|P4−P7|+|P4−P6|+|P4−P3|=G the gross radial gradient. This algorithm produces the gross radial gradient (G) across the central pixel (P4)—see FIG. 8.
4) All image pixels with edge values (G) of greater than or equal to 8 are assigned to the PUPIL_EDGE class—see FIG. 9. The pupil edge value of 8 was selected using empirical methods as a value discriminating valid edge pixels.
5) In order to locate an area of PUPIL_EDGE pixels large enough to be the actual pupil, a spiral search is initiated from the centre of the image (or the centre of a valid pupil from the previous frame to improve the speed of location), is used to locate the first PUPIL_EDGE pixel and this is assumed to lie on the pupil boundary—see FIG. 10.
6) When the search locates a PUPIL_EDGE pixel—see FIG. 10, All adjoining PUPIL_EDGE pixels are connected using a recursive flood fill algorithm The fill algorithm also tracks the numbers and extents of the adjoining pixels, from which the width and height of pupil region are derived—see FIG. 11. If the fill connects more than 16 pixels, the area is designated as being the pupil boundary area and the algorithm continues to step 7. If the fill connects less than 16 pixels, the area is designated as being too small to be the pupil and the spiral search (5) continues outwards until another PUPIL EDGE region is found or the extents of the image are reached. If the pupil boundary area has not been located by the end of the spiral search, the algorithm restarts at step 1 with the next captured image.

In steps 5 and 6, every time the spiral search hits a PUPIL_EDGE the region is flood filled to try to find a region large enough to be the pupil. When the pupil is identified, the spiral search exits.

Recursive Flood Fill

Figure 12:
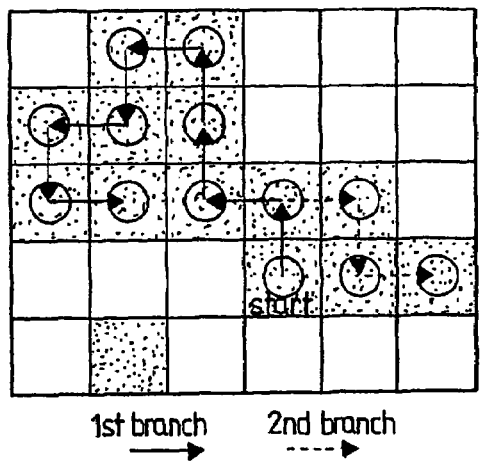
FIG. 12 is a table illustrating a recursive flood-fill algorithm.

The fill algorithm sets the target pixel and tests each of its four neighbours, in north-west-south-east order, for another PUPIL EDGE pixel. As soon as such a pixel is found, the algorithm re-calls itself with this new pixel as its target. An enlarged view of a typical fill pattern is shown in FIG. 12. The first branch is filled by the routine calling itself nine ties and stops when no further PUPIL EDGE pixels are found, the second branch (dotted arrows) search then starts. In this way, the routine continues until all adjoining PUPIL EDGE pixels have been set—see FIG. 12.

Figure 13:
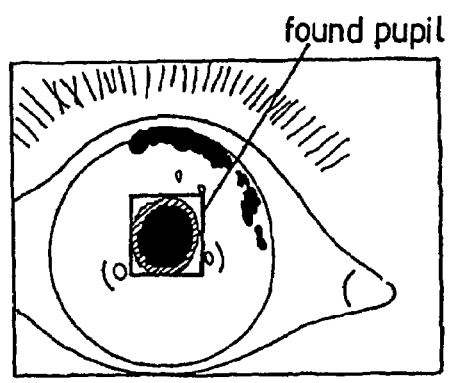
FIG. 13 shows the image of FIG. 11 with the rectangular dimension of the pupil identified.
Figure 14:
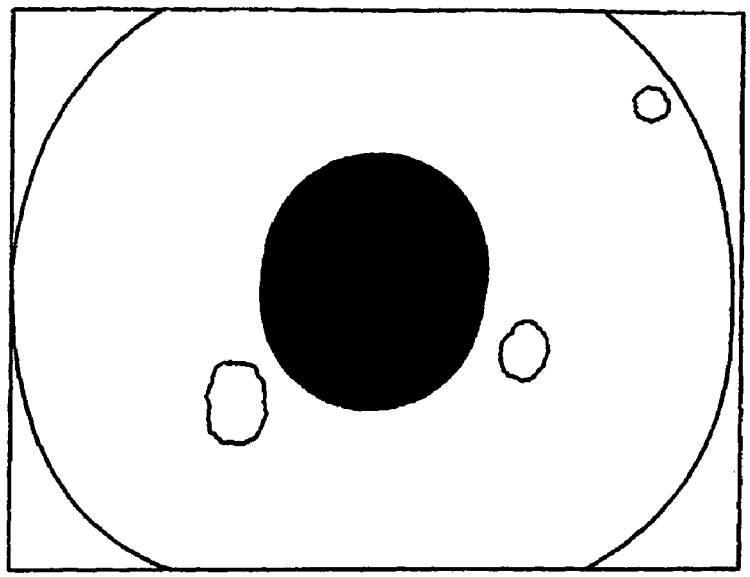
FIG. 14 shows an image of a part of an eye close to the pupil when subjected to highlights from infra-red LED's of the pupilometer.

The rectangular dimension of the pupil boundary area is calculated from the extents of the flood fill and an ellipse consisting of thirty-two points is fitted inside this rectangle. If twelve or more of these points hit a PUPIL EDGE pixel the region is classified as the PUPIL and the range detection phase begins; if not the search re-starts with the next captured image. The pupil diameter is defined as the maximum diameter of the ellipse—see FIG. 13.

Ranging

When a valid pupil has been classified it is known that the highlights from the infra red LED's will appear in the image within close proximity to the pupil. Therefore to improve speed of calculation and removal of artefacts from eyelids etc, only the area around the pupil is searched.

A first procedure for ranging is illustrated in FIGS. 14 to 18, and is described below. The search identifies discrete groups of pixels which could belong to valid highlights With reference to FIG. 14, a search area 84 wide by 64 pixels high centred around the pupil is scanned to identify pixels with values of greater than or equal to the previously assigned threshold Tlight, these are classed as HIGHLIGHT_TEST pixels. When such a pixel is found, a flood fill of adjoining HIGHLIGHT_TEST pixels is initiated during which the number of pixels and centre co-ordinates of the fill area is recorded.

Figure 15:
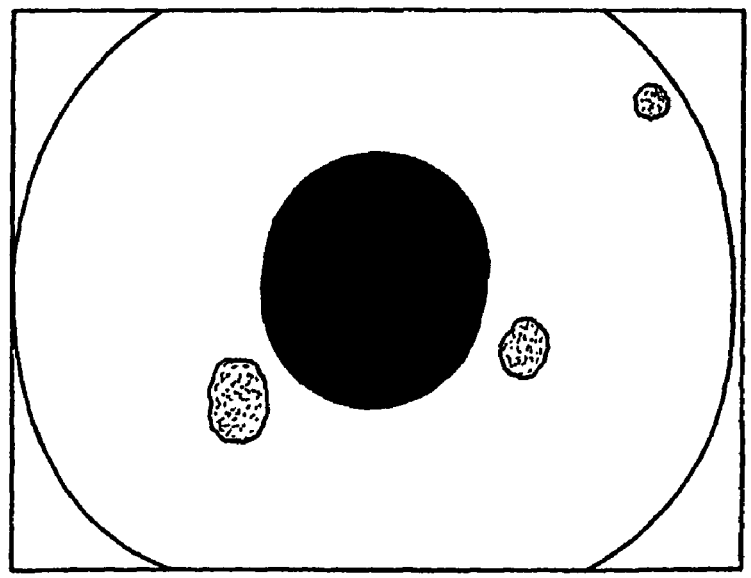
FIG. 15 shows the image of FIG. 14 with possible highlights marked.

Possible highlights are defined as fill areas with pixel counts within the range 4 to 256 pixels, and FIG. 15 illustrates the identification of such areas. These areas are designated as possible valid highlights and their centre co-ordinates and pixel counts are stored in an array. In order to minimise memory usage, a maximum of 16 areas are allowed.

Figure 16:
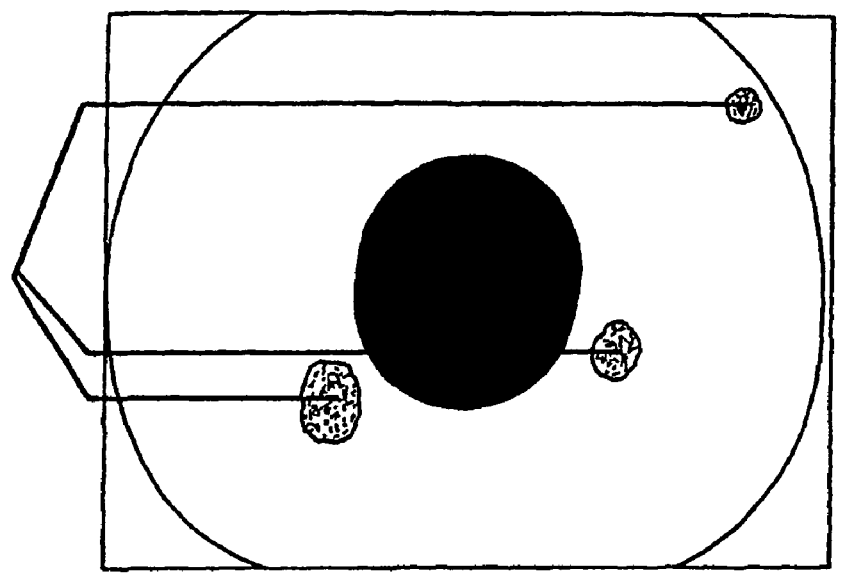
FIG. 16 shows the comparison of highlight vertical co-ordinates in FIG. 15.

As shown in FIG. 16, when the whole search area has been scanned and two or more possible highlight areas identified, the vertical positions of all areas are compared in order to identify the two areas with the closest vertical alignment.

Figure 17:
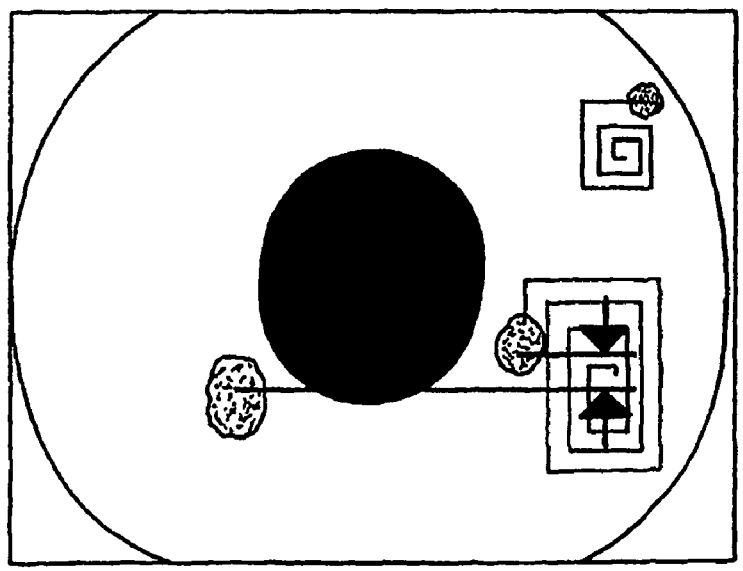
FIG. 17 shows identification of the highlights of FIG. 16 with the closest vertical alignment.

FIG. 17 shows the identification of two such areas.

If less than two or no suitably aligned highlights have been identified, the algorithm is unable to derive range information, and a "range error" signal is generated and the pupil detection phase restarts on the next captured image.

Figure 18:
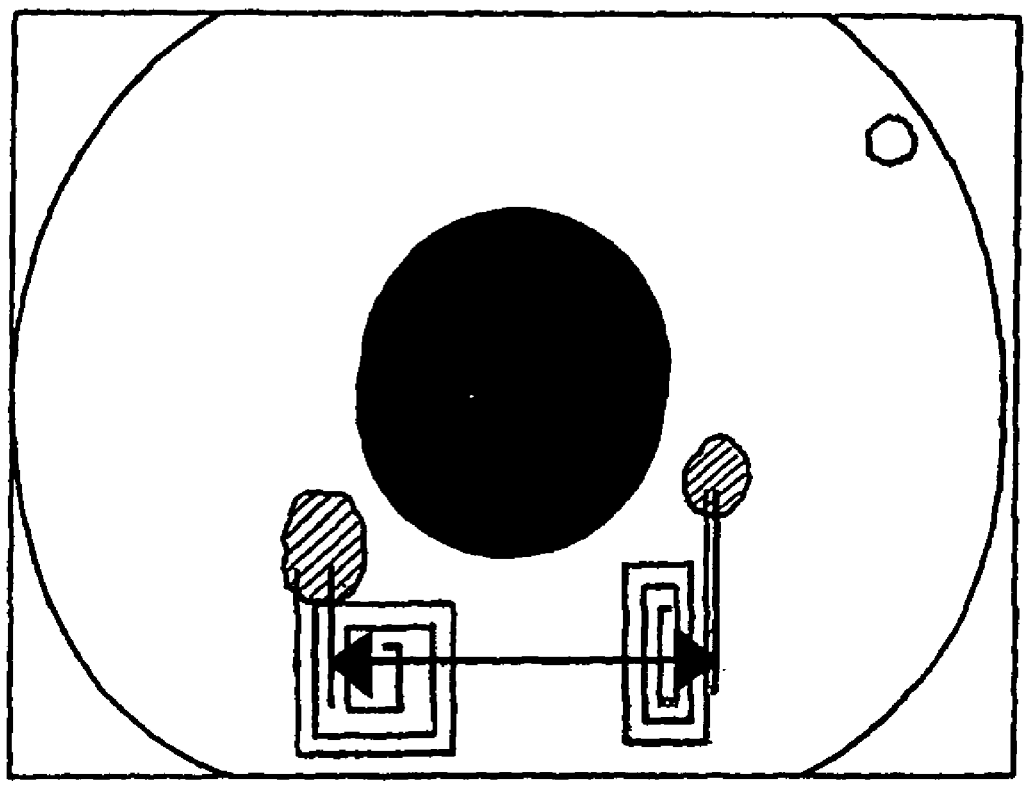
FIG. 18 shows the image of FIG. 17 with the distance between the two valid highlights marked.

FIG. 18 illustrates the final range step, where with both valid highlight areas identified, the horizontal distance between their centres and the geometry of the infra-red LED position and the light emitted thereby allow the software to calculate accurately the distance of the pupilometer from the surface of the patients eyeball. If the distance to the eyeball is outside the valid detection range $r_{min}$ to $r_{max}$, the algorithm will generate a "range error" signal and the pupil detection phase restarts on the next captured image.

A second procedure for ranging is illustrated in FIGS. 24 to 28 is described below.

Figure 24:
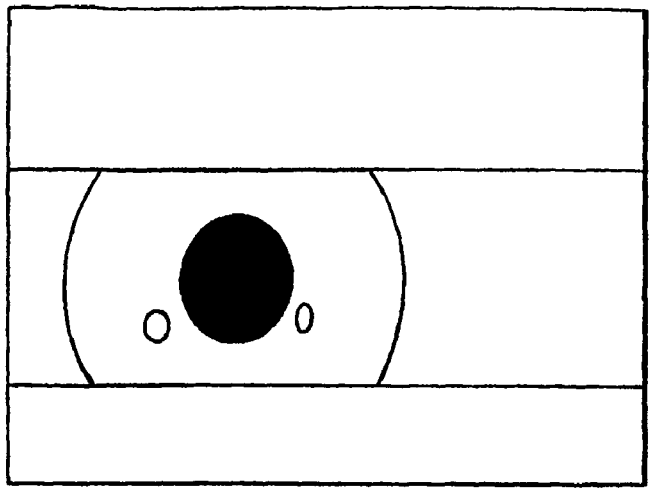
FIG. 24 shows an image of a part of an eye close to the pupil when subjected to highlights from infra-red LED's of the pupilometer.

With reference to FIG. 24, an area twelve pixels above and below the pupil is scanned to find the BRIGHTEST pixel level.

Figure 25:
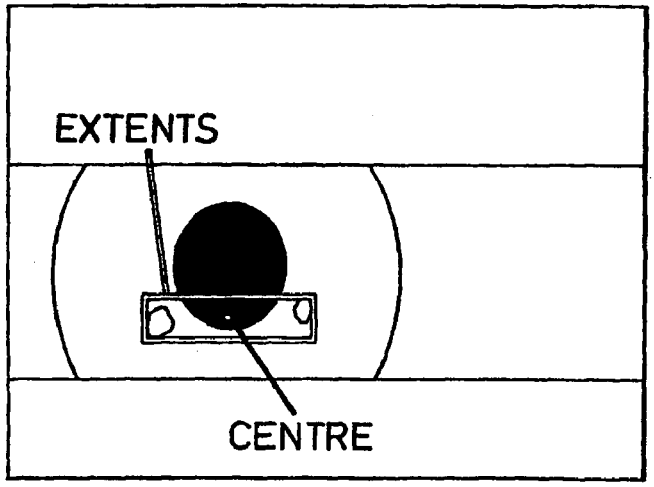
FIG. 25 shows the image of FIG. 14 with the highlights marked.

With reference to FIG. 25, the area is rescanned and pixels with a value greater than BRIGHTEST-8 are marked as HIGHLIGHT pixels. The maximum x/y extent of these HIGHLIGHT pixels is recorded and the centre of the extents is calculated.

Centre $X$=(Max Highlight $X$–Min Highlight $X$)/2

Centre $Y$=(Max Highlight $Y$–Min Highlight $Y$)/2

Figure 26:
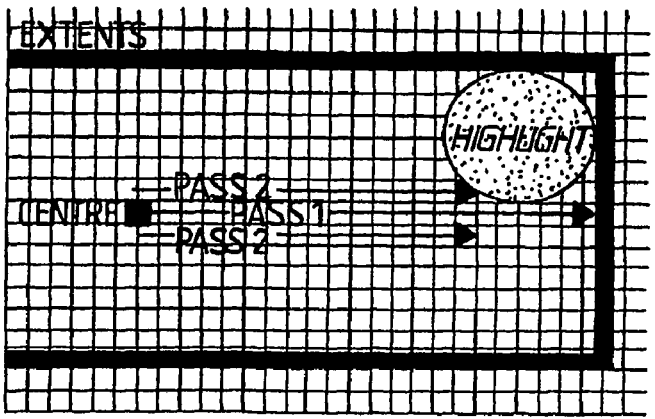
FIG. 26 is a schematic representation of the marked highlights of FIG. 15.

FIG. 26 illustrates horizontal lines of pixels, starting from the centre pixel (PASS 1) and expanding one pixel vertically above and below the centre line (PASS 2 . . . ), which are scanned to the right hand extents until a HIGHLIGHT pixel is found.

Figure 27:
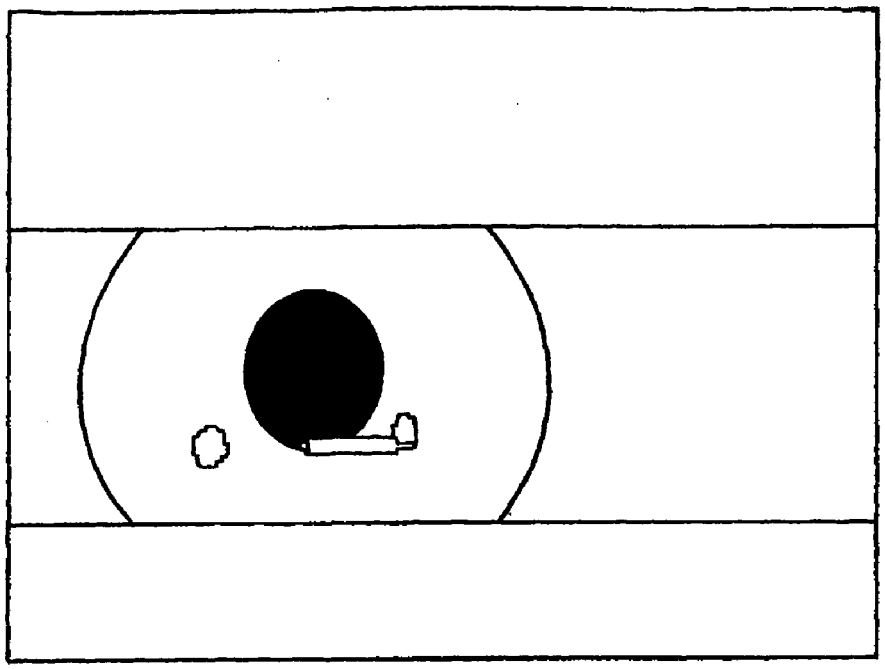
FIG. 27 shows the image of FIG. 14 with the distance from the highlight to the centre marked.

FIG. 27 shows the HIGHLIGHT area flood-filled, with the centre of the area calculated from the extents of the flood-fill. Steps 16 and 17 are then repeated for the pixels on the left-hand side of the centre pixel.

Figure 28:
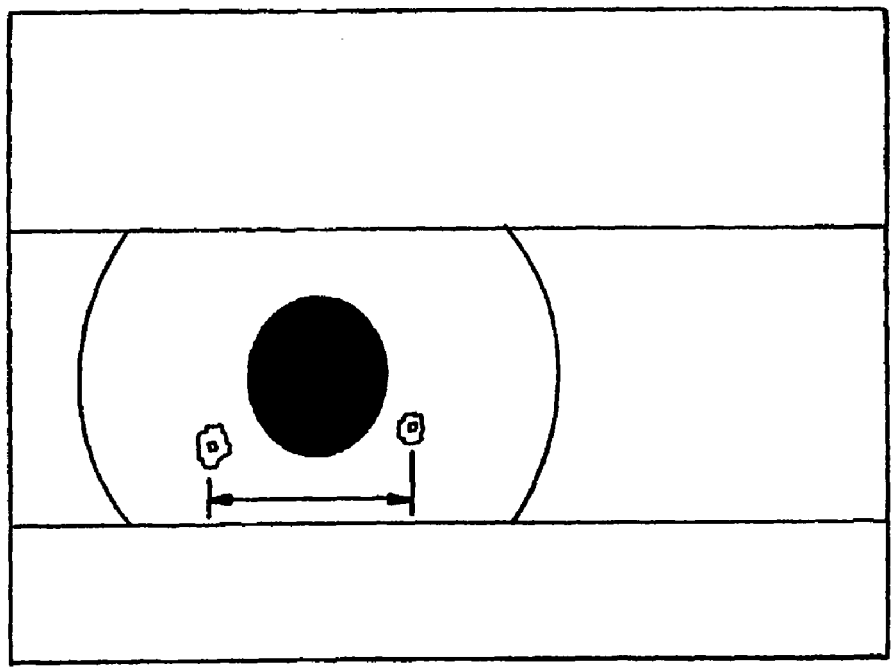
FIG. 28 shows the image of FIG. 14 with the distance between the two highlights marked.

FIG. 28 illustrates the next step, where with both highlight areas identified, the horizontal distance between their centres is used as a measure of the range.

Stimulation

A lookup table is used to calculate the absolute pupil diameter in millimetres from the measures of pupil pixel diameter and range. When a valid pupil measurement has been made, the system can start a stimulation cycle to obtain the pupil constriction response curve after stimulus by a bright white light source. The LED 14 generates white light In a stimulation cycle the LED 14 is energised. In this example, the period during which the LED 14 is energised for approximately 600 ms.

Figure 19:
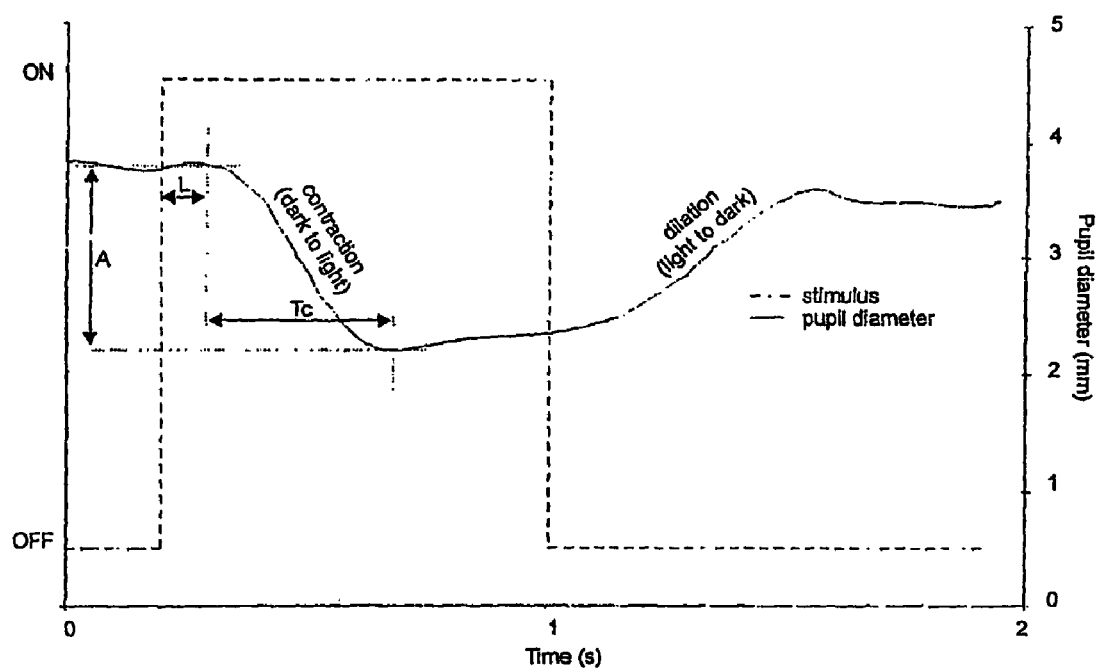
FIG. 19 is a graph showing the reaction over time of a pupil diameter to a light stimulation.

During the stimulation cycle, the pupil diameter is continuously measured and recorded using the above described algorithm whilst the white LED is energised. A graph, illustrated in FIG. 19, of the pupil diameter is then drawn, a typical response curve is shown below.

Where the following measurements can be taken;

| L | Latency (ms) | Time between start of stimulus and beginning of contraction |
|---|---|---|
| A | Contraction amplitude (mm) | Difference between the mean post-stimulus diameter and minimum per-stimulus diameter |
| Tc | Contraction time (ms) | Time from end of latency to minimum pupil diameter |

In the case of a hand-held pupilometer as described with reference to FIGS. 20 to 22, the graph may be displayed on the display 102 of the hand-held device, or on a VDU.

The response curve can be used in itself in diagnosis, or the response curve can form part of an expert system, which may generate a diagnosis.

The invention allows for the calculation of the distance between the surface of the eyeball and the camera. No spacer of fixed dimension is required to establish a pre-determined distance between the camera and the surface of the eyeball.

Furthermore, there is no requirement for a patient being examined to keep its head still, and look in a fixed direction. The pupil of the patient being examined need not be aligned with the centre of the camera. The pupilometer of the invention functions as long as the infra-red LED's produce highlights in the vicinity of the pupil As well as permitting examination of semi-conscious or unconscious patients, the pupilometer can be used on patients who cannot necessarily follow instructions, for example children, impaired individuals, animals, etc. Rather than assuming that the pupil is a dark area in the centre of the image, the pupil finds the dark pupil anywhere in the image.

The invention provides a simple and relatively low cost device for use in a variety of operational situations. Further, it provides a reliable and objective means of assessing pupil response.

The invention claimed is:

1. A pupilometer comprising image capturing means, illumination means comprising two spaced apart light sources, stimulation means, and image processing software, wherein said illumination means generates and emits light of a first wavelength, and said stimulation means generates and emits light of a second wavelength, and wherein said illumination means is arranged to one or both sides of said image capturing means and, in use, shines light towards an eyeball, wherein the image processing software receives data from the image capturing means, and by processing said data according to an algorithm establishes the distance between the surface of the eyeball and the image capturing means, wherein establishing the distance between the surface of the eyeball and the image capturing means includes detecting the pupil and measuring the size of the detected pupil.

2. A pupilometer according to claim 1, wherein establishing the distance between the surface of the eyeball and the image capturing means includes finding highlights on the surface of the eyeball generated by the illumination means and calculating the distance between said highlights.

3. A pupilometer according to claim 1, wherein the wavelength of the light generated by said illumination means is in the infra-red spectrum.

4. A pupilometer according to claim 3, wherein each light source is an infra-red light emitting diode.

5. A pupilometer according to claim 1, wherein the image capturing means has an optical axis, and wherein the two spaced apart light sources shine light in a direction substantially parallel to the optical axis of the image capturing means.

6. A pupilometer according to claim 1, wherein said stimulation means comprises a light emitting diode generating and emitting light in the visible spectrum.

7. A pupilometer according to claim 1, wherein said image capturing means comprises a camera.

8. A pupilometer according to claim 1, further comprising an optical filter mounted on the image capturing means.

9. A pupilometer according to claim 8, wherein the optical filter passes only light of the first wavelength.

10. A pupilometer according to claim 7, wherein said camera generates a video signal.

11. A pupilometer according to claim 7, wherein said camera is a complementary metal oxide semiconductor device.

12. A pupilometer according to claim 1, wherein said image detection means further includes a micro-controller including a micro-processor.

13. A pupilometer according to claim 1, further comprising an analogue to digital converter arranged between said image capturing means and said micro-controller.

14. A pupilometer according to claim 1, further comprising memory means.

15. A pupilometer according to claim 1, further comprising data input means and display means.

16. A pupilometer according to claim 1, further comprising an interface for linking said pupilometer to an external computer.

17. A pupilometer according to claim 1, wherein said pupilometer is a hand-held device, wherein said hand-held device mounts said image capturing means, illumination means, stimulation means, image processing software, data input means, display means, a computer interface, said hand-held device including a hand grip.

18. A pupilometer according to claim 17, wherein, in use, the user views the image of the eye displayed on the display means, the image having been captured by said image capturing means and processed by said image processing software.

19. A pupilometer according to claim 1, further comprising a power supply consisting of a battery.

\* \* \* \* \*